United States Patent [19]

Hope

[11] Patent Number: Plant 5,675

[45] Date of Patent: Feb. 25, 1986

[54] KALANCHOE PLANT NAMED MONTERAY

[75] Inventor: Claude Hope, Cartago, Costa Rica

[73] Assignee: Pan American Plant Company, Parrish, Fla.

[21] Appl. No.: 594,489

[22] Filed: Mar. 27, 1984

[51] Int. Cl.[4] ..... A01H 5/00

[52] U.S. Cl. ..... Plt./68

[58] Field of Search ..... Plt./68

*Primary Examiner*—Robert E. Bagwill

*Attorney, Agent, or Firm*—Schwartz, Jeffery, Schwaab, Mack, Blumenthal & Evans

[57] ABSTRACT

A new and distinct cultivar of Kalanchoe plant named Monteray characterized by its large salmon colored flowers and floriferous habit; compact and freely branching habit; large, medium green succulent foliage, and by its adaptability to production in 10–15 cm. pots.

1 Drawing Figure

1

The present invention relates to a new and distinctive cultivar of Kalanchoe plant, botanically known as Kalanchoe, named Monteray.

The new cultivar is a product of a planned breeding program. Monteray following discovery and initial selection was designed by the code number KLV80-166N upon being received by Pan American Plant Co., West Chicago, Ill. in 1980. The basic objective of the breeding program resulting in the new cultivar was to create a new Kalanchoe cultivar having salmon flower color, prolific flowering, compact habit, and the ability to produce commercially acceptable quality in a year round kalanchoe program.

The new cultivar was originated from a self-pollination of a cultivar which is unknown at this time. The cultivar was developed in a controlled breeding program at Linda Vista S.A., Cartago, Costa Rica.

Monteray was discovered and selected by me or a technician working under my direction, as a flowering plant within the progeny of the stated self in a field of seedlings in Cortago, Costa Rica. Asexual reproduction of the new cultivar by stem cuttings, as performed by me at Pan American Plant Co., West Chicago, Ill. and Parrish, Fla., has demonstrated that the combination of characteristics as herein disclosed for the new cultivar are firmly fixed and are retained through successive generations of asexual reproduction.

Monteray has not been observed under all possible environmental conditions. The phenotype may vary significantly with variations in environment such as temperature, light intensity and day length. The following observations, measurements and values describe the new cultivar as grown in Parrish, Fla., under greenhouse conditions which closely approximate those generally used in commercial practice.

The following traits have been repatedly observed and are determined to be basic characteristis of Monteray, which in combination distinguish this Kalanchoe as a new and distinct cultivar:

(1) Numerous, large salmon flowers.

(2) Compact habit, and average growth rate as compared to other cultivars.

(3) Freely branching with shoots formed at every node.

(4) Suitable for production in 10–15 cm. pots, and flowering from 12 weeks under favorable conditions to 14 weeks under less favorable conditions such as high temperature and light conditions.

2

(5) Highly floriferous, with a mass of flowers formed at every shoot.

(6) To reduce peduncle elongation after flower initiation, plants can be treated with B-9.

(7) Large medium green, succulent foliage with crenate margins.

The accompanying photographic drawing shows a typical specimen plant of the new cultivar. The colors appearing in the photograph are as true as possible with color illustrations of this type.

In the following description, color references are made to The Royal Horticultural Society Colour Chart (R.H.S.), except where general colors of ordinary significance are referred to. Color values are taken under 7000 ft. candles of natural light at approximately 10:00 A.M. in Parrish, Fla.

Botanical classification: Kalanchoe, cv. Monteray.

Parentage: Unknown at this time.

Propagation: The new cultivar holds its distinguishing characteristics through successive propagations by leaf cuttings and by division of shoots.

A. *Type cutting.*—Tip cuttings with stems up to 2 cm. long.

B. *Time to root.*—10 days at 21° C. in summer to 14 days at 21° C. in winter.

C. *Rooting habit.*—Fibrous, many fine roots.

Plant description:

A. *Form.*—Upright, compact growth; scheduling practices can produce small plants in 10 cm. pots or large plants in 15 cm. pots.

B. *Habit of growth.*—Average growth rate for this type of plant. Shoots are formed at every node.

C. *Foliage description.*—Leaves simple, opposite, generally symmetrical. (1) Size: Average full grown leaf of a flowering plant in a 10 cm. pot is 60–85 mm. long and 60–70 mm. wide. Plants in larger pots have larger full grown leaves. (2) Shape: Ovate; apex obtuse, base truncate. (3) Texture: Glabrous, coriaceous, succulent. (4) Margin: Crenate, irregular. (5) Color: Young foliage top side, 137C, under side, 137C. Mature foliage top side 137A, under side 137C.

Flowering description:

A. *Flowering habit.*—Inflorescence of each shoot is formed by dichotomous branching, starting with opening of the terminal flower of the main axis followed by terminal flowers of the side branches of the inflorescence. Opening of new buds will continue for 2 months or more. Individual flowers will last two weeks or more after opening.

B. *Natural flowering season.*—January. Flowering time under controlled daylength at 32° C. in summer is 14 weeks; in winter at 21° C., 12 weeks. Flowering time depends on temperature, light intensity and other growing conditions.

C. *Flower buds.*—Oblong, developing to tubular as petals mature. Sheathed with 4 green sepals. Corolla at maturity is about 14 mm. long. (1) Size: Up to 14 mm. long. (2) Shape: Oblong. (3) Rate of opening: Normal.

D. *Flowers borne.*—Compound dichosial cyme on strong peduncles. Peduncle length depends upon growing conditions and B-9 application. Pedicels up to 5 mm. long.

E. *Quantity of flowers.*—Very floriferous with new buds continuing to develop.

F. *Petals.*—(1) Shape: Obovate, apex cuspidate. (2) Color: Top side when opening, 43C, fading to 39B; under side, 37D. (3) Number and size of petals: 4, united in corolla; petals up to 6 mm. in diameter, total flower diameter up to 18 mm.

G. *Reproductive organs.*—(1) Stamens: 8 in number. (a) Anther shape: Flat, elliptical. (b) Filament color: Yellow. (c) Pollen color: Yellow. (2) Pistils: (a) Stigma shape: Flat, crystalline. (b) Style color: Greenish-white. (c) Ovaries: 4 celled, 7 mm. long, green.

Disease resistance: No known Kalanchoe diseases observed to date.

General observations: Monteray is characterized by an abundance of bright salmon flowers positioned above a compact, freely branching plant. The medium green leaves are large and very succulent. Monteray has an average 12 week flowering response and is adaptable to production in 10–15 cm. pots.

I claim:

1. A new and distinct cultivar of Kalanchoe plant named Monteray, as described and illustrated, and particularly characterized by its large salmon colored flowers and floriferous habit; compact and freely branching habit; large, medium green succulent foliage, and by its adaptability to production in 10–15 cm. pots.

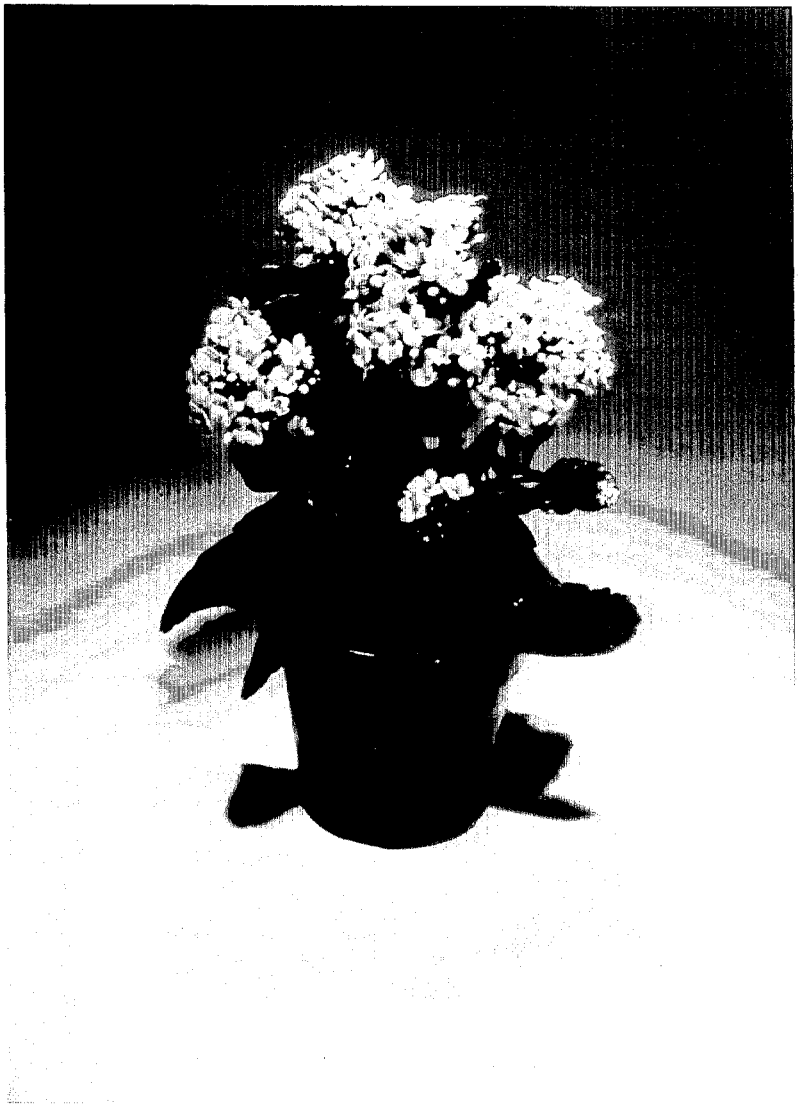

* * * * *